United States Patent
Xu

(10) Patent No.: US 10,407,403 B2
(45) Date of Patent: Sep. 10, 2019

(54) PREPARATION METHOD OF COBIMETINIB

(71) Applicant: SUZHOU MIRACPHARMA TECHNOLOGY CO., LTD., Suzhou (CN)

(72) Inventor: Xuenong Xu, Suzhou (CN)

(73) Assignee: Suzhou Miracpharma Technology Co., Ltd., Suzhou (CN)

( * ) Notice: Subject to any disclaimer, the term of this patent is extended or adjusted under 35 U.S.C. 154(b) by 0 days.

(21) Appl. No.: 15/995,098

(22) Filed: May 31, 2018

(65) Prior Publication Data

US 2018/0273506 A1 Sep. 27, 2018

Related U.S. Application Data

(63) Continuation of application No. PCT/CN2016/098853, filed on Sep. 13, 2016.

(30) Foreign Application Priority Data

Dec. 9, 2015 (CN) .......................... 2015 1 0906811

(51) Int. Cl.
C07D 401/04 (2006.01)
A61K 31/4523 (2006.01)

(52) U.S. Cl.
CPC ........ C07D 401/04 (2013.01); A61K 31/4523 (2013.01)

(58) Field of Classification Search
CPC .................................................. C07D 401/00
USPC ........................................................ 546/208
See application file for complete search history.

(56) References Cited

FOREIGN PATENT DOCUMENTS

| CN | 101605540 A | 12/2009 |
|---|---|---|
| CN | 104725352 A | 6/2015 |
| CN | 104837826 A | 8/2015 |
| WO | 2007044515 A1 | 4/2007 |
| WO | 2008124085 A2 | 10/2008 |
| WO | 2015032840 A1 | 3/2015 |

OTHER PUBLICATIONS

Hughes; Org. Process Res. Dev. 2016, 20, 1855-1869. (Year: 2016).*
Rice, K.D. et al., "Novel Carboxamide-Based Allosteric MEK Inhibitors: Discovery and Optimization Efforts toward XL518 (GDC-0973)", ACS Med. Chem. Lett., vol. 3, No. 5, Apr. 9, 2012 (Apr. 9, 2012), pp. 416-421, and schemes 1-3.

* cited by examiner

Primary Examiner — Daniel R Carcanague
(74) Attorney, Agent, or Firm — Schwegman Lundberg & Woessner, P.A.

(57) ABSTRACT

The present invention discloses a preparation method of cobimetinib (XL518, GDC-0973) (I). The preparation steps include: taking (2S)-2-piperidinecarboxylic acid as the raw material, performing acyl cyanation, hydrolysis, esterification and Boc protection to obtain an intermediate [2-oxo-2-((2S)-1-tert-butoxycarbonylpiperidin-2-yl)]acetate, performing an addition reaction, a reduction reaction and a cyclization reaction on the intermediate to obtain an intermediate (2S)-1-tert-butoxycarbonyl-2-(3-hydroxyazetidin-3-yl)piperidine, and performing a condensation reaction with a side chain to obtain the cobimetinib (I). The preparation method has the advantages of accessible raw materials, simple technique, high economy and environment friendliness, and is suitable for industrial production.

10 Claims, No Drawings

PREPARATION METHOD OF COBIMETINIB

CROSS REFERENCE TO RELATED APPLICATIONS

This application is a continuation of PCT/CN2016/098853 filed Sep. 13, 2016, which claims priority to CN 201510906811.2 filed Dec. 9, 2015, both of which are incorporated herein by reference.

TECHNICAL FIELD

The present invention belongs to the technical fields of organic synthesis route design, and preparation of active pharmaceutical ingredients and intermediates thereof, and particularly relates to a preparation method of a drug cobimetinib for treating melanoma.

BACKGROUND ART

Cobimetinib (XL518, GDC-0973) is an oral small molecule MEK inhibitor developed by Roche. Cobimetinib is designed to selectively block the activity of the MEK protein, thereby blocking its downstream signaling pathways. The drug was first approved by the Swiss Bureau of Drug Administration in August 2015 and was approved by the US FDA to come into the market in November 2015 for the treatment of unresectable or metastatic melanoma in combination with Zelboraf. Since the drug does not have a standard Chinese name, the applicant transliterated it as "kabitini".

The chemical name of cobimetinib (I) is: [3,4-difluoro-2-[(2-fluoro-4-iodophenyl)amino]phenyl][3-hydroxy-3-(2 S)-2-piperidyl-1-azacyclo-butyl]methanone, and its structural formula is:

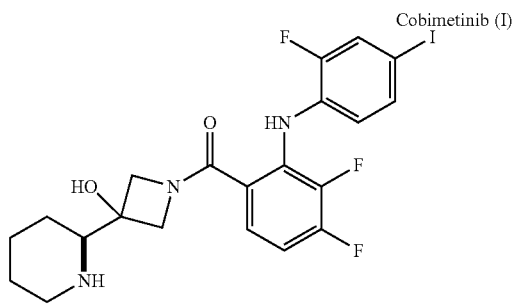

Cobimetinib (I)

The synthesis of cobimetinib (I) has been reported in the literature. From its structural analysis, it can be seen that the difficulty in the synthesis of the compound is mainly reflected in how to obtain the chiral group in the molecular structure quickly, economically and with high purity. There are two main routes for the preparation of the compound at present.

PCT patents WO2007044515, WO2008076415, WO2008124085, and "ACS Medicinal Chemistry Letters" 2012 Vol. 3, No. 5, pages 416-421 et al. reported a synthesis method of cobimetinib (I). The above literature has some changes in the side chain linking method, such as: firstly forming a trifluorophenyl acylate, and then substituting one of fluorine atoms with another aniline containing fluorine and iodine to complete the linking of the entire side chain (fractional-step method); or firstly preparing benzoic acid or acyl chloride containing two substituted benzene ring side chains, and performing amidation reaction to obtain cobimetinib (one-step method). However, the core chiral intermediate (II) is prepared by firstly preparing a racemate and then performing chiral resolution by using a resolving agent (R)-alpha-methoxy-alpha-trifluoromethylphenyl-acetyl chloride, thereby obtaining the desired S-configuration target intermediate (II). From the perspective of the reaction process and yield, due to the need for repeated resolutions of at least 3 times, the steps are quite complex, a large amount of resolving agents and other auxiliary materials are needed, and the highest resolution yield is only 50%, thereby limiting the industrialization of the process.

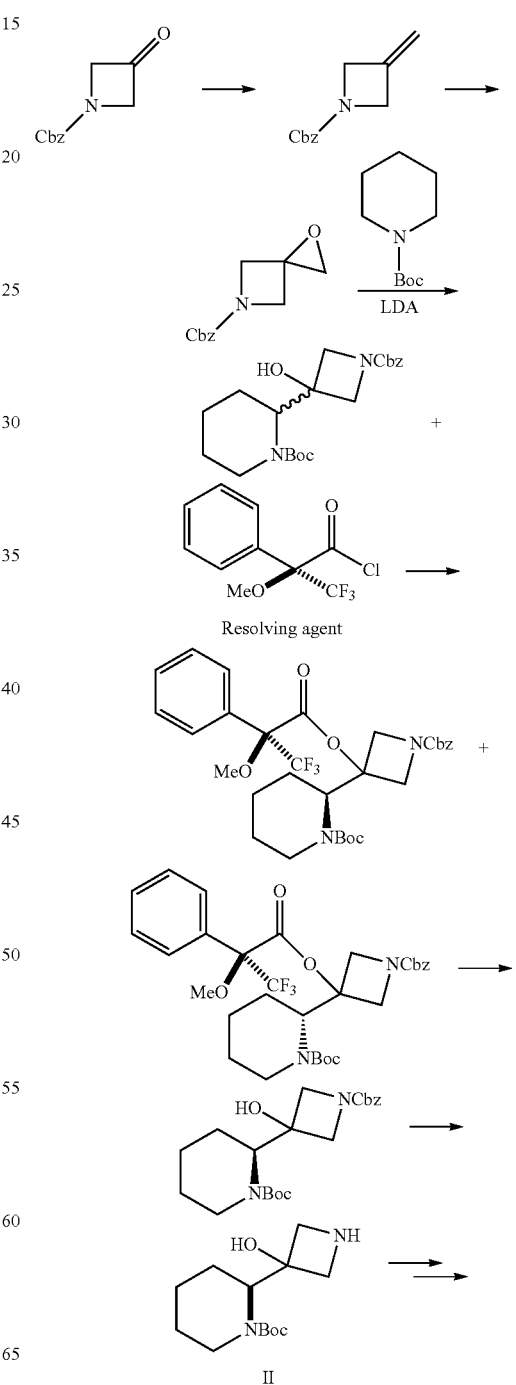

II

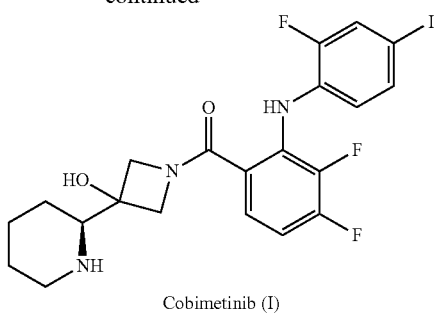

Cobimetinib (I)

The PCT patent WO2014059422 describes another preparation method of cobimetinib (I) and analogs thereof, which abandons the low-efficient resolution method, but uses chiral amino alcohols as a chiral inducing reagent, making it more convenient and economical for obtaining chirality. However, the chiral inducing reagent (raw material) containing nitrile group is difficult to obtain, the strong alkali lithium diisopropylamide is unstable, and ultralow temperature (−78° C.) and absolutely water-free oxygen-free reaction conditions are needed, thereby also limiting the industrialization prospect of the synthesis route.

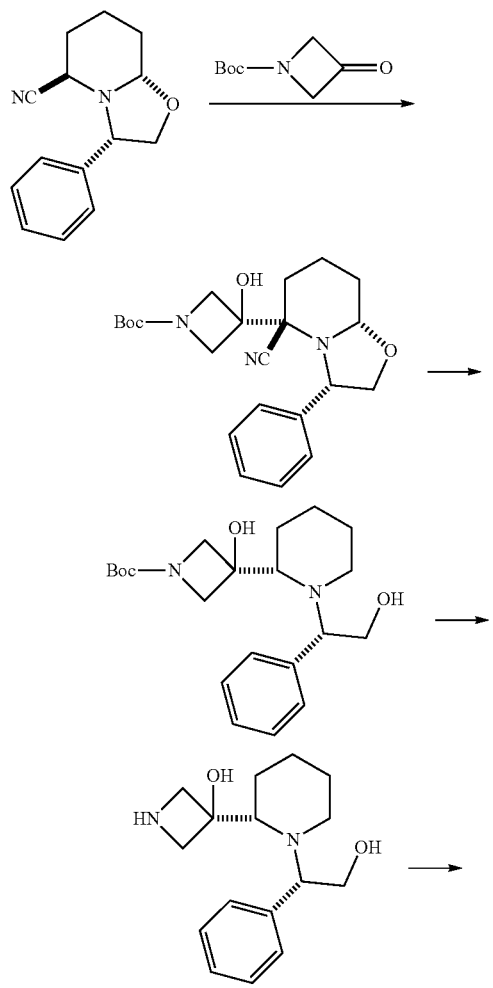

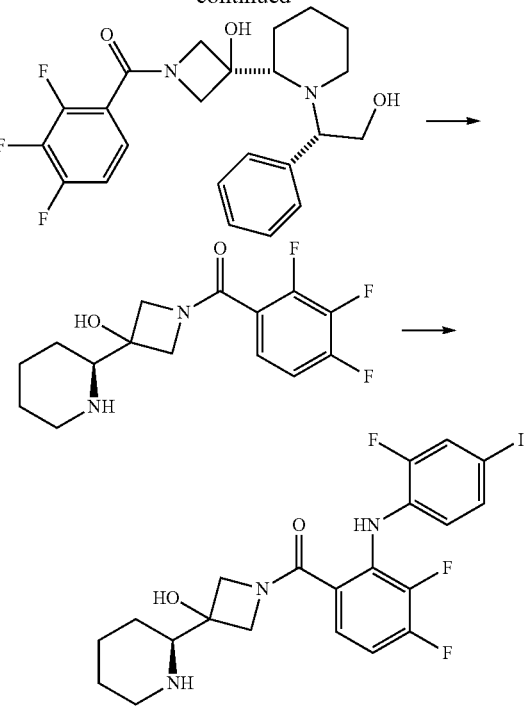

Cobimetinib (I)

In view of the defects in the existing process, the development of a simple, economical, environment-friendly and high-quality preparation technology, in particular the seek for a technology capable of adapting to industrial production, has important practical significance on the improvement of the economic and social benefits of the drug.

SUMMARY OF THE INVENTION

The present invention aims to provide a preparation method of cobimetinib, which has the advantages of accessible raw materials, simple technique, high economy and environment friendliness and is suitable for industrial production.

In order to achieve the above objects, the present invention adopts the following main technical scheme: a preparation method of cobimetinib (I),

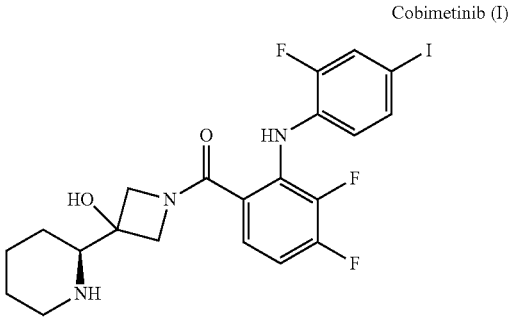 [SMILES: O=C(c1ccc(F)c(F)c1Nc1ccc(I)cc1F)N1CC(O)([C@@H]2CCCCN2)C1]

Cobimetinib (I)

the preparation steps include: performing an acyl cyanation reaction on (2S)-2-piperidinecarboxylic acid (III) with thionyl chloride, a cyanation reagent and a phase-transfer catalyst, performing cyano hydrolysis on an obtained product, performing an esterification reaction with alcohol, and protecting the piperidine nitrogen by using di-tert-butyl dicarbonate to obtain [2-oxo-2-((2S)-1-tert-butoxycarbonylpiperidin-2-yl)]acetate (IV); performing an addition reaction on the [2-oxo-2-((2S)-1-tert-butoxycarbonylpiperidin-2-yl)]acetate (IV) and nitromethane under the action of a catalyst to obtain [2-hydroxy-2-((2S)-1-tert-butoxycarbonylpiperidin-2-yl)-3-nitro]propionate (V); sequentially performing ester group and nitro reduction reactions on the [2-hydroxy-2-((2S)-1-tert-butoxycarbonylpiperidin-2-yl)-3-nitro]propionate (V) to obtain [2-hydroxy-2-((2S)-1-tert-butoxycarbonylpiperidin-2-yl)-3-amino]propanol (VI); performing a cyclization reaction on the [2-hydroxy-2-((2 S)-1-tert-butoxycarbonylpiperidin-2-yl)-3-amino]propanol (VI) under the actions of an azo reagent and an organic phosphine reagent to obtain (2S)-1-tert-butoxycarbonyl-2-(3-hydroxyazetidin-3-yl)piperidine (II); and performing a condensation reaction on the (2S)-1-tert-butoxycarbonyl-2-(3-hydroxyazetidin-3-yl)piperidine (II) and 3,4-difluoro-2-[(2-fluoro-4-iodophenyl)amino]benzoic acid under the actions of a condensing agent and an alkali accelerator; and deprotecting the compound resulting from the condensation reaction, to obtain cobimetinib (I).

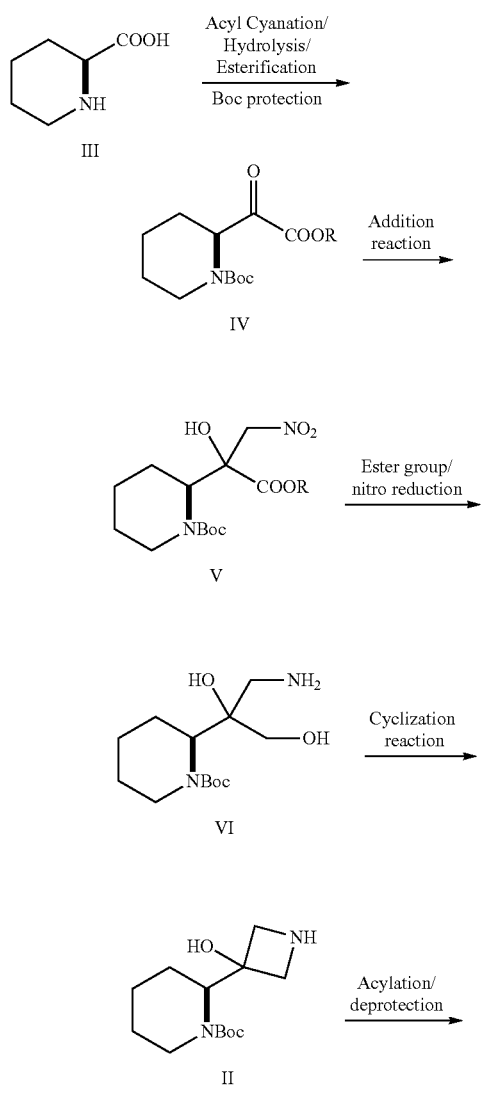

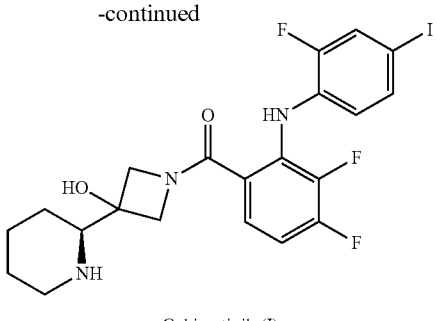

Cobimetinib (I)

Wherein the alcohol used in the esterification reaction is methanol, ethanol, n-propanol, isopropanol, allyl alcohol or benzyl alcohol, and the obtained corresponding ester is methyl ester, ethyl ester, n-propyl ester, isopropyl ester, allyl ester or benzyl ester.

Besides, the present invention also provides the following dependent technical schemes:

The cyanation reagent in the acyl cyanation reaction is sodium cyanide, zinc cyanide, cuprous cyanide or trimethylsilyl cyanide, preferably cuprous cyanide.

The phase-transfer catalyst used in the acyl cyanation reaction is benzyl triethylammonium chloride, tetrabutylammonium bromide, tetrabutylammonium chloride, tetrabutylammonium hydrogen sulfate, trioctyl methyl chloride ammonium, dodecyltrimethylammonium chloride or tetradecyltrimethylammonium chloride, preferably tetrabutylammonium bromide or tetrabutylammonium chloride.

The temperature of the acyl cyanation reaction is 50-150° C., preferably 90-100° C.; and the reaction solvent is benzene/water, toluene/water, xylene/water or 1,2-dichloroethane/water in a volume ratio of 1-5/1, preferably toluene/water in a volume ratio of 2/1.

The catalyst of the cyano hydrolysis reaction is sodium chloride and sulfuric acid, and the reaction temperature is 45-50° C.

The alcohol used in the esterification reaction is methanol, ethanol, n-propanol, isopropanol, allyl alcohol or benzyl alcohol, preferably methanol or ethanol.

The temperature of the esterification reaction is 50-90° C., preferably 70-80° C.

The catalyst of the piperidin amino protection reaction is N,N-diethyl-1,2-diamine.

The catalyst of the addition reaction is sodium methoxide, sodium ethoxide, potassium carbonate, cesium carbonate, sodium hydroxide, potassium hydroxide, sodium tert-butoxide or potassium tert-butoxide, preferably sodium methoxide, sodium ethoxide, or potassium hydroxide.

The temperature of the addition reaction is 0-100° C., preferably 50-60° C.

The reducing agent of the ester group reduction reaction is sodium borohydride, potassium borohydride, borane or lithium tetrahydroaluminate, preferably sodium borohydride or lithium tetrahydroaluminate.

The reducing agent of the nitro reduction reaction is iron, zinc, tin dichloride, lithium tetrahydroaluminate or hydrogen, preferably lithium tetrahydroaluminate or hydrogen.

When the reducing agent of the nitro reduction reaction is hydrogen, the catalyst to be added is palladium carbon or Raney nickel.

The azo reagent of the cyclization reaction is diethyl azodicarboxylate, diisopropyl azodicarboxylate, di-tert-butyl azodicarboxylate or di-p-chlorobenzyl azodicarboxylate, preferably diethyl azodicarboxylate.

The organic phosphine reagent of the cyclization reaction is triphenylphosphine, tri-n-butylphosphine, trimethylphosphine, (cyanomethylene)tri-n-butylphosphorane or (cyanomethylene)trimethylphosphorane, preferably triphenylphosphine.

The mole ratio of the raw material [2-hydroxy-2-((2S)-1-tert-butoxycarbonylpiperidin-2-yl)-3-amino]propanol (VI) to the azo reagent to the organic phosphine reagent in the cyclization reaction is 1:1-2:1-2, preferably 1:1.1-1.5: 1.1-1.5.

The temperature of the cyclization reaction is room temperature, and the solvent is dichloromethane, dioxane, acetonitrile or tetrahydrofuran, preferably tetrahydrofuran.

The condensing agent of the condensation reaction is N,N,-dicyclohexylcarbodiimide, carbonyldiimidazole, N,N'-diisopropylcarbodiimide, 1-hydroxy-benzotriazole, O-benzotriazol-N,N,N',N'-tetramethyluronium tetrafluoroborate, O-(7-azobenzotriazol)-N,N,N',N'-tetramethyluronium hexafluorophosphate, benzotriazol-N,N,N',N'-tetramethyluronium hexafluorophosphate, benzotriazol-1-yloxytris(dimethylamino)phosphonium hexafluorophosphate or benzotriazol-1-yl-oxytripyrrolidinophosphonium hexafluorophosphate, preferably benzotriazol-1-yloxytris(dimethylamino)phosphonium hexafluorophosphate or benzotriazol-1-yl-oxytripyrrolidinophosphonium hexafluorophosphate.

The alkali accelerator of the condensation reaction is triethylamine, pyridine, 2,6-lutidine, 4-dimethylaminopyridine, N-methylmorpholine, N-ethylmorpholine, diisopropylethylamine, 1,5-diazabicyclo[4.3.0]-non-5-ene, 1,8-diazabicyclo[5.4.0]-undec-7-ene or 1,4-diazabicyclo[2.2.2] octane, preferably diisopropylethylamine.

The solvent of the condensation reaction is toluene, xylene, ethyl acetate, isopropyl acetate, butyl acetate, chloroform, dimethyl sulfoxide, N,N-dimethylformamide or acetonitrile, preferably N,N-dimethylformamide or acetonitrile.

The temperature of the condensation reaction is 0-120° C., preferably 40-55° C.

Compared with the prior art, the preparation method of cobimetinib (I) according to the present invention implements the preparation of the target compound through well-known unit reactions by using the accessible chiral source reagent and other common reagents. The preparation method has the characteristics of accessible raw materials, simple technique, high economy and environment friendliness, thereby facilitating the industrial production of the active pharmaceutical ingredient, and promoting the development of its economy and technology.

DETAILED DESCRIPTION OF THE INVENTION

A further nonrestrictive detailed description of the technical scheme of the present invention will be given below in combination with several preferred embodiments. For the starting material (2S)-2-piperidinecarboxylic acid (III) and a Boc protection method thereof, refer to "Journal of the American Chemical Society, 132(35), 12216-12217; 2010" or "Tetrahedron: Asymmetry, 14(12), 1685-1689; 2003", et al. As for the side chain 3,4-difluoro-2-[(2-fluoro-4-iodophenyl)amino] benzoic acid, refer to "ACS Medicinal Chemistry Letters, 3(5), 416-421; 2012" for the related preparation method.

Embodiment 1

Adding (2S)-2-piperidinecarboxylic acid (III) (6.45 g, 50 mmol) and thionyl chloride (15 mL) into a reaction bulb, performing a reflux reaction for 3 hours, and performing vacuum distillation to remove the excessive thionyl chloride, thereby obtaining brown oil; at room temperature, adding 50 mL of toluene, 25 mL of water and 0.1 g of a phase-transfer catalyst tetrabutylammonium bromide into the oil in a fume hood, adding cuprous cyanide (8.05 g, 90 mmol) while stirring, heating to 90-100° C., and stirring to react for 2-3 hours; cooling, standing for stratification, extracting a water phase with toluene for 2 times, reducing the pressure to recover the solvent, adding sodium chloride (0.32 g, 5.5 mmol), water (1.0 g, 55 mmol) and sulfuric acid (5.4 g, 55 mmol) into the obtained oil, maintaining the temperature at 45-50° C., reacting for 2-4 hours, adding 20 mL of esterification reagent methanol, heating to 70-75° C., reacting for 3 hours, and performing TLC detection to finish the reaction; performing concentration under reduced pressure, dissolving the residue with dichloromethane, washing sequentially with water, a 10% sodium bicarbonate solution and a saturated saline solution, drying with anhydrous sodium sulfate, performing concentration, dissolving the obtained thick oil in 25 mL of methanol, dropwisely adding a 50 mL methanol solution of di-tert-butyl dicarbonate (8.72 g, 40 mmol) at room temperature, reacting for 2 hours, adding N,N-diethyl-1,2-diamine (0.88 g, 10 mmol), and continuing stirring to react for 1 hour, thereby completing the reaction; and performing concentration under reduced pressure, dissolving the residue with ethyl acetate, sequentially washing with water, 5% hydrochloric acid and a saturated saline solution, performing stratification, drying an organic phase with anhydrous sodium sulfate, performing concentration, recrystallizing an obtained crude product with n-hexane and ethyl acetate (1:1, V/V), and performing vacuum drying to obtain 7.45 g of an off-white solid methyl [2-oxo-2-((2S)-1-tert-butoxycarbonylpiperidin-2-yl)]acetate (IV), wherein the yield is 55.0%; MS (EI): m/z 272 (M+H).

Embodiment 2

In the same manner as in Embodiment 1, ethanol is used as the esterification reagent to obtain 7.35 g of an off-white solid ethyl [2-oxo-2-((2S)-1-tert-butoxycarbonylpiperidin-2-yl)]acetate (IV), wherein the yield is 51.4%; MS (EI): m/z 286 (M+H).

Embodiment 3

Adding methyl [2-oxo-2-((2 S)-1-tert-butoxycarbonylpiperidin-2-yl)]acetate (IV) (2.71 g, 10 mmol), sodium methoxide (0.65 g, 12 mmol) and nitromethane (15 mL) into a reaction bulb, heating to 50-60° C., stirring to react for 5-7 hours, and performing TLC detection to finish the reaction; reducing the pressure to recover the excessive nitromethane, adding dichloromethane into the residue, washing with water and a saturated saline solution, and drying with anhydrous sodium sulfate; and performing concentration to obtain 2.96 g of a light yellow solid methyl [2-hydroxy-2-((2S)-1-tert-butoxycarbonylpiperidin-2-yl)-3-nitro]propionate (V), wherein the yield is 89.4%; MS (EI): m/z 333 (M+H).

Embodiment 4

Adding ethyl [2-oxo-2-((2S)-1-tert-butoxycarbonylpiperidin-2-yl)]acetate (IV) (2.85 g, 10 mmol), potassium hydroxide (0.67 g, 12 mmol), nitromethane (1.22 g, 20 mmol) and ethanol (25 ml) into a reaction bulb, heating to 50-60° C., stirring to react for 5-7 hours, and performing TLC detection to finish the reaction; reducing the pressure to recover the solvent, adding dichloromethane into the residue, washing with water and a saturated saline solution, and drying with anhydrous sodium sulfate; and performing concentration to obtain 2.92 g of a light yellow solid ethyl [2-hydroxy-2-((2 S)-1-tert-butoxycarbonylpiperidin-2-yl)-3-nitro]propionate (V), wherein the yield is 84.4%; MS (EI): m/z 347 (M+H).

Embodiment 5

Adding methyl [2-hydroxy-2-((2S)-1-tert-butoxycarbonylpiperidin-2-yl)-3-nitro]propionate (V) (1.66 g, 5 mmol) and methanol (50 mL) into a reaction bulb, adding sodium borohydride (0.38 g, 10 mmol) in batches, maintaining the temperature at 20-30° C., and stirring to react for 6 hours; performing filtration to remove small amounts of insoluble substances, and transferring the filtrate into a hydrogenation reactor; adding 5% palladium carbon (0.15 g), maintaining the temperature at 35-40° C. and the hydrogen pressure at 2 Kg, and reacting for 5-6 hours; performing filtration, recovering the catalyst, and performing concentration to precipitate a solid; and recrystallizing a crude product with ethyl acetate/n-hexane (½) to obtain 1.07 g of [2-hydroxy-2-((2S)-1-tert-butoxycarbonylpiperidin-2-yl)-3-amino]propanol (VI), wherein the yield is 78.1%; MS (EI): m/z 275 (M+H).

Embodiment 6

Adding ethyl [2-hydroxy-2-((2S)-1-tert-butoxycarbonylpiperidin-2-yl)-3-nitro]propionate (V) (1.73 g, 5 mmol) and tetrahydrofuran (25 ml) into a dry reaction bulb, adding lithium tetrahydroaluminate (0.62 g, 16 mmol) in batches, after the addition is finished, maintaining at room temperature, and stirring to react for 5-6 hours; quenching the reaction with 20% sodium hydroxide, extracting with ethyl acetate for 3 times, merging organic phases, washing with a saturated saline solution once, and performing concentration; and recrystallizing a crude product with ethyl acetate/n-hexane (½) to obtain 1.12 g of [2-hydroxy-2-((2S)-1-tert-butoxycarbonylpiperidin-2-yl)-3-amino]propanol (VI), wherein the yield is 81.7%; MS (EI): m/z 275 (M+H).

Embodiment 7

Adding [2-hydroxy-2-((2S)-1-tert-butoxycarbonylpiperidin-2-yl)-3-amino]propanol (VI) (1.37 g, 5 mmol), triphenylphosphine (1.58 g, 6 mmol) and tetrahydrofuran (25 mL) into a reaction bulb, dropwisely adding a tetrahydrofuran 25 mL solution of diethyl azodiformate (1.04 g, 6 mmol) in an ice bath, after the addition is finished, heating to room temperature, stirring to react for 3-4 hours, and performing TLC detection to complete the reaction; performing reduced pressure distillation, dissolving the residue with ethyl acetate and n-hexane, performing filtration to remove the insoluble substance, washing the filtrate with water, and drying with anhydrous sodium sulfate; and performing concentration, and recrystallizing a crude product with n-hexane/methanol to obtain 1.08 g of an off-like solid (2S)-1-tert-butoxycarbonyl-2-(3-hydroxyazetidin-3-yl)piperidine (II), wherein the yield is 84.4%; ¹H NMR (400 MHz, CD3OD) 4.31 (m, 1H), 3.85 (brs, 1H), 3.71 (d, J=8.8 Hz, 1H), 3.54 (d, J=9.2 Hz, 1H), 3.42 (d, J=9.6 Hz, 1H), 3.39 (d, J=9.2 Hz, 1H), 3.37 (brs, 1H), 1.90-1.97 (m, 2H), 1.55-1.78 (m, 6H), 1.47 (s, 9H); MS (EI): m/z 257 (M+H).

Embodiment 8

Adding 3,4-difluoro-2-[(2-fluoro-4-iodophenyl)amino]benzoic acid (1.96 g, 5 mmol) and N,N-dimethylformamide (25 mL) into a reaction bulb, and dropwisely adding an N,N-dimethylformamide 25 mL solution of benzotriazol-1-yl-oxytripyrrolidino-phosphonium hexafluorophosphate (2.6 g, 5 mmol) within 30 minutes; adding (2S)-1-tert-butoxycarbonyl-2-(3-hydroxyazetidin-3-yl)piperidine (II) (1.92 g, 7.5 mmol) and diisopropylethylamine (1.29 g, 10 mmol); heating to 45-50° C., stirring to react for 3-4 hours, and performing TLC detection to complete the reaction; adding ethyl acetate and a 10% sodium hydroxide solution into the reaction solution, stirring for 15 minutes, and separating out an organic layer; washing the organic layer with water for 3 times, washing with a saturated saline solution once, and drying with anhydrous sodium sulfate; and performing concentration, adding a 4N dioxane hydrogen chloride solution (25 mL) into an obtained solid, heating to 55-60° C., stirring to react for 2-4 hours, cooling to room temperature, performing concentration under reduced pressure, and recrystallizing a crude product with ethyl acetate/n-hexane (1/1) to obtain 1.86 g of an off-white solid cobimetinib (I), wherein the yield is 70.1%; M.p. 170-172° C.; ¹H NMR (400 MHz, CDCl3) 8.39 (m, 1H), 7.40 (dd, 1H), 7.37 (dd, 1H), 7.12 (m, 1H), 6.81 (m, 1H), 6.62 (m, 1H), 4.09 (m, 3H), 3.96 (m, 1H), 3.09 (dd, 1H), 2.69 (dd, 1H), 2.63 (m, 2H), 1.76 (m, 1H), 1.64-1.22 (m, 7H); MS (EI): m/z 532 (M+H).

It should be noted that the foregoing embodiments are merely to illustrate the technical concept and features of the present invention, and the purpose of the embodiments is to allow those skilled in the art to understand the contents of the present invention and implement the present invention accordingly, and the foregoing embodiments are not intended to limit the protection scope of the present invention. All equivalent changes or modifications made according to the spirit of the present invention shall fall within the protection scope of the present invention.

I claim:
1. A preparation method of cobimetinib,

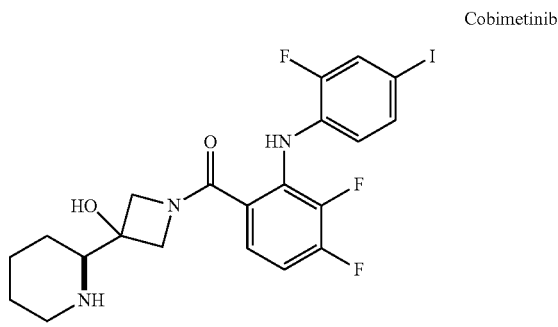

Cobimetinib the preparation steps including: performing an acyl cyanation reaction on (2S)-2-piperidinecarboxylic acid with thionyl chloride, a cyanation reagent and a phase-transfer catalyst, performing cyano hydrolysis on an obtained product, performing an esterification reaction with alcohol, and protecting the piperidine nitrogen by using di-tert-butyl dicarbonate to obtain [2-oxo-2-

((2S)-1-tert-butoxycarbonylpiperidin-2-yl)]acetate; performing an addition reaction on the [2-oxo-2-((2S)-1-tert-butoxycarbonylpiperidin-2-yl)]acetate and nitromethane under the action of a catalyst to obtain [2-hydroxy-2-((2S)-1-tert-butoxycarbonylpiperidin-2-yl)-3-nitro]propionat; sequentially performing ester group and nitro reduction reactions on the [2-hydroxy-2-((2S)-1-tert-butoxycarbonylpiperidin-2-yl)-3-nitro] propionate to obtain [2-hydroxy-2-((2S)-1-tert-butoxycarbonylpiperidin-2-yl)-3-amino]propanol; performing a cyclization reaction on the [2-hydroxy-2-((2S)-1-tert-butoxycarbonylpiperidin-2-yl)-3-amino]propanol under the actions of an azo reagent and an organic phosphine reagent to obtain (2S)-1-tert-butoxycarbonyl-2-(3-hydroxyazetidin-3-yl)piperidine; and performing a condensation reaction on the (2S)-1-tert-butoxycarbonyl-2-(3-hydroxyazetidin-3-yl)piperidine and 3,4-difluoro-2-[(2-fluoro-4-iodophenyl)amino]benzoic acid under the actions of a condensing agent and an alkali accelerator; and deprotecting the compound resulting from the condensation reaction, to obtain cobimetinib; wherein the alcohol in the esterification reaction is methanol, ethanol, n-propanol, isopropanol, allyl alcohol or benzyl alcohol.

2. The preparation method of cobimetinib according to claim 1, wherein the cyanation reagent in the acyl cyanation reaction is sodium cyanide, zinc cyanide, cuprous cyanide or trimethylsilyl cyanide; the phase-transfer catalyst used in the acyl cyanation reaction is benzyl triethylammonium chloride, tetrabutylammonium bromide, tetrabutylammonium chloride, tetrabutylammonium hydrogen sulfate, trioctyl methyl chloride ammonium, dodecyltrimethylammonium chloride or tetradecyltrimethylammonium chloride; the temperature of the acyl cyanation reaction is 50-150° C.; and the reaction solvent is benzene/water, toluene/water, xylene/water or 1,2-dichloroethane/water in a volume ratio of 1-5/1.

3. The preparation method of cobimetinib according to claim 1, wherein the catalyst of the cyano hydrolysis reaction is sodium chloride and sulfuric acid, and the reaction temperature is 45-50° C.

4. The preparation method of cobimetinib according to claim 1, wherein the catalyst of the addition reaction is sodium methoxide, sodium ethoxide, potassium carbonate, cesium carbonate, sodium hydroxide, potassium hydroxide, sodium tert-butoxide or potassium tert-butoxide; and the temperature of the addition reaction is 0-100° C.

5. The preparation method of cobimetinib according to claim 1, wherein the reducing agent of the ester group reduction reaction is sodium borohydride, potassium borohydride, borane or lithium tetrahydroaluminate; and the reducing agent of the nitro reduction reaction is iron, zinc, tin dichloride, lithium tetrahydroaluminate or hydrogen.

6. The preparation method of cobimetinib according to claim 1, wherein the azo reagent of the cyclization reaction is diethyl azodicarboxylate, diisopropyl azodicarboxylate, di-tert-butyl azodicarboxylate or di-p-chlorobenzyl azodicarboxylate; and the organic phosphine reagent of the cyclization reaction is triphenylphosphine, tri-n-butylphosphine, trimethylphosphine, (cyanomethylene)tri-n-butylphosphorane or (cyanomethylene)trimethylphosphorane.

7. The preparation method of cobimetinib according to claim 1, wherein the mole ratio of the raw material [2-hydroxy-2-((2S)-1-tert-butoxycarbonylpiperidin-2-yl)-3-amino]propanol to the azo reagent to the organic phosphine reagent in the cyclization reaction is 1:1-2:1-2.

8. The preparation method of cobimetinib according to claim 1, wherein the condensing agent of the condensation reaction is N,N,-dicyclohexylcarbodiimide, carbonyldiimidazole, N,N'-diisopropylcarbodiimide, 1-hydroxy-benzotriazole, O-benzotriazol-N,N,N',N'-tetramethyluronium tetrafluoroborate, O-(7-azobenzotriazol)-N,N,N',N'-tetramethyluronium hexafluorophosphate, benzotriazol-N,N,N',N'-tetramethyluronium hexafluorophosphate, benzotriazol-1-yloxytris(dimethylamino)phosphonium hexafluorophosphate or benzotriazol-1-yl-oxytripyrrolidinophosphonium hexafluorophosphate.

9. The preparation method of cobimetinib according to claim 1, wherein the alkali accelerator of the condensation reaction is triethylamine, pyridine, 2,6-lutidine, 4-dimethylaminopyridine, N-methylmorpholine, N-ethylmorpholine, diisopropylethylamine, 1,5-diazabicyclo[4.3.0]-non-5-ene, 1,8-diazabicyclo[5.4.0]-undec-7-ene or 1,4-diazabicyclo[2.2.2]octane.

10. The preparation method of cobimetinib according to claim 1, wherein the solvent of the condensation reaction is toluene, xylene, ethyl acetate, isopropyl acetate, butyl acetate, chloroform, dimethyl sulfoxide, N,N-dimethylformamide or acetonitrile; and the temperature of the condensation reaction is 0-120° C.

* * * * *